(12) United States Patent
Cronin

(10) Patent No.: US 7,118,590 B1
(45) Date of Patent: Oct. 10, 2006

(54) RADIATION APPLICATOR

(75) Inventor: Nigel Cronin, Bath (GB)

(73) Assignee: Microsulis Limited, Denmead (GB)

( * ) Notice: Subject to any disclaimer, the term of this patent is extended or adjusted under 35 U.S.C. 154(b) by 0 days.

(21) Appl. No.: 09/914,375

(22) PCT Filed: Feb. 25, 2000

(86) PCT No.: PCT/GB00/00682

§ 371 (c)(1),
(2), (4) Date: Jan. 15, 2002

(87) PCT Pub. No.: WO00/49957

PCT Pub. Date: Aug. 31, 2000

(30) Foreign Application Priority Data

Feb. 25, 1999 (GB) ................................. 9904373.9

(51) Int. Cl.
*A61N 1/06* (2006.01)
(52) U.S. Cl. ........................................ 607/105; 606/33
(58) Field of Classification Search ................ 607/100, 607/101, 154–156, 96, 98; 606/32–3, 41
See application file for complete search history.

(56) References Cited

U.S. PATENT DOCUMENTS

| | | |
|---|---|---|
| 4,409,993 A | 10/1983 | Furihata |
| 4,643,186 A | 2/1987 | Rosen et al. |
| 4,662,383 A | 5/1987 | Sogawa et al. |
| 4,865,047 A | 9/1989 | Chou et al. |
| 4,967,765 A | 11/1990 | Turner et al. |
| 5,026,959 A | 6/1991 | Ito et al. |
| 5,129,396 A | 7/1992 | Rosen et al. |
| 5,220,927 A | 6/1993 | Astrahan et al. |
| 5,249,585 A | 10/1993 | Turner et al. |
| 5,300,099 A | 4/1994 | Rudie |
| 5,344,435 A | 9/1994 | Turner et al. |
| 5,344,441 A | 9/1994 | Gronauer |
| 5,370,676 A | 12/1994 | Sozanski et al. |
| 5,370,677 A | 12/1994 | Rudie et al. |
| 5,628,771 A | 5/1997 | Mizukawa et al. |

(Continued)

FOREIGN PATENT DOCUMENTS

FR  2 679 456  7/1991

(Continued)

OTHER PUBLICATIONS

IEICE Transactions on Communications, vol. E78-B, No. 6, pp. 845-850, Jun. 1995.

(Continued)

*Primary Examiner*—Michael Peffley
*Assistant Examiner*—Aaron Roane
(74) *Attorney, Agent, or Firm*—Cesari and McKenna, LLP

(57) ABSTRACT

Radiation applicators comprise an elongate device having an antenna (240, 340) at their tip for coupling radiation into biological tissue and a dielectric body (250, 350) surrounding the antenna so as to encompass substantially the whole of the near-field region of the antenna and/or to enhance transmission of radiation in the forward direction. The body (250, 350) may be cylindrical with the antenna (240, 340) along its axis. The antenna may be λ/2 in length and λ/2 in radius. The tip (270) of the antenna (240) may be rounded hemispherical with radius λ/2 to enhance forward transmission of radiation. The dielectric constant (ε) of the body (250, 350) is as high as possible to reduce its diameter at a desired operating frequency but may be matched to the surrounding tissue by another layer of dielectric material (380) with a value (ε) intermediate that of the core (360) of the body (350) and the tissue.

20 Claims, 2 Drawing Sheets

U.S. PATENT DOCUMENTS

| | | | |
|---|---|---|---|
| 5,693,082 | A | 12/1997 | Warner et al. |
| 6,047,216 | A * | 4/2000 | Carl et al. ................... 607/101 |
| 6,097,985 | A * | 8/2000 | Kasevich et al. ........... 607/102 |
| 6,287,302 | B1 * | 9/2001 | Berube ......................... 606/33 |
| 6,325,796 | B1 * | 12/2001 | Berube et al. ................. 606/33 |

FOREIGN PATENT DOCUMENTS

| | | |
|---|---|---|
| FR | 2 699 069 | 12/1992 |
| JP | 60-43982 | 10/1985 |
| JP | 2-289272 | 11/1990 |
| JP | 4-28377 | 1/1992 |
| JP | 8-187297 | 7/1996 |
| JP | 01320070 A | 12/1999 |
| WO | WO 81/03616 | 12/1981 |
| WO | WO 89/02292 | 3/1989 |
| WO | WO 89/11311 | 11/1989 |
| WO | WO 91/02560 | 3/1991 |
| WO | WO 93/20768 | 10/1993 |
| WO | WO 95/05869 | 3/1995 |

OTHER PUBLICATIONS

IEEE Transactions on Microwave Theory and Techniques, vol. 39, No. 7, pp. 1178, Jul. 1991.
1990 International Symposium Digest. Anetannas and Propagation. Institute of Electrical and Electronics Engineers. Merging Technologies for the 90s, pp. 1233-1236, vol. 3.
1990 IEEE MTT-S International Microwave Symposium Digest, pp. 545-548, vol. 1, 1990, 3 vol. 1371, pp.
Physics in Medicine and Biology, vol. 35, No. 6, pp. 761-779, Jun. 1990.
IEE Colloquium on Medical Applications of Microwaves, pp. 1/1-4/2/1-4, 1988, 52 pp.
Proceedings of the 1985 International Symposium on Antennas and Propagation, pp. 751-754, vol. 3, 1985.
IEEE Transactions on Microwave Theory and Techniques, vol. MTT-34, No. 5, pp. 631-635, May 1986.
1985 IEEE—MTT-S International Microwave Symposium Digest, pp. 196-199, 1985, v+743 pp.
1985 IEEE—MTT-S International Microwave Symposium Digest, pp. 86-89, 1985, v+743 pp.
1984 International Symposium on Electromagnetic Compatibility, pp. 366-371, vol. 1 1984, 2 vol. Xvi+956 pp.
Proceedings of the Tenth Annual Northeast Bioengineering Conference, pp. 94, 1982, xi+356 pp.
IEEE Transactions on Microwave Theory and Techniques, vol. MTT-28, No. 12, pp. 1418-1422, Dec. 1980.
1980 IEEE MTT-S International Microwave Symposium Digest, pp. 351-354, 1980, xx+511 pp.
Radio Science, vol. 12, No. 6, suppl., pp. 111-122, Nov.-Dec. 1977.
1977 International Microwave Symposium Digest, pp. 364-367, 1977.
Br. J. Hosp. Med., Feb. 5-18, 1992; 47 (3): 192-6.
1998 IEEE—MTT-S International Microwave Symposium Digest, Pt. vol. 2, pp. 755-758 vol. 2, 1998.
IEEE Transactions on Biomedical Engineering, vol. 45, No. 7, pp. 885-890, Jul. 1998.
Proceedings of the IEEE 23rd Northeast Bioengineering Conference, pp. 46-47, 1997.
1995 IEEE MTT-S International Microwave Symposium Digest, Pt. vol. 1, pp. 303-306, vol. 1, 1995.
IEEE Transactions on Microwave Theory and Techniques, vol. 41, No. 6-7, pp. 1135-1142, Jun.-Jul. 1993.
1991 IEEE MTT-S International Microwave Symposium Digest, Jun. 10-14, 1991, 787-790.
Conference Proceedings. 21st European Microwave Conference, Microwave '91, pp. 1427-1432, 1991, 2 vol.
IEEE Transactions on Microwave Theory and Techniques, vol. 39, No. 6, pp. 1048-1054, Jun. 1991.
International Journal of Hyperthermia, vol. 6, No. 6, pp. 997-1004, Nov.-Dec. 1990.
Proceedings of 2nd International Symposium on Recent Advances in Microwave Technology, pp. 363-365, 1989.
International Journal of Hyperthermia, vol. 6, No. 4, pp. 745-753, Jul.-Aug. 1990.
1989 International Symposium Digest: Antennas and Propagation, pp. 540-543, vol. 1.
Proceedings of the Eighth Annual Conference of the IEEE/Engineering in Medicine and Biology Society, pp. 1454-1457, vol. 3, 1986, 3 vol. 1952 pp.
International Journal of Hyperthermia, vol. 3, No. 1, pp. 37-47, Jan.-Feb. 1987.
Journal of Microwave Power, vol. 19, No. 4, pp. 259-267, Dec. 1984.
International Journal of Radiation Oncology Biology Physics, vol. 10, No. 11, pp. 2155-2162, Nov. 1984.
IEEE Transactions on Microwave Theory and Techniques, vol. MTT-30, No. 11, pp. 2005-2008, Nov. 1982.
IEEE Transactions on Microwave Theory and Techniques, vol. MTT-27, No. 9, pp. 767-799, Sep. 1979.
Proceedings of the 8th European Microwave Conference, pp. 559-563, 1978, 835 pp.
Lancet, Oct. 14, 1995, pp. 1003-1004.
Br. J. Obstet. Gynaecol., Jul. 1999, pp. 684-694.
Lancet, Nov. 27, 1999, pp. 1859-1863.
Contrib. Gynecol. Obstet., 2000 pp. 91-120.
Contrib. Gynecol. Obstet., 2000 pp. 145-153.
Fertil. Sterilisation, Mar. 2000, pp. 598.
Curr. Opin. Obstet. Gynecol., Aug. 2000, pp. 293-296.
Clin. Obstet. Gynecol, Sep. 2000, pp. 575-583.
BJOG., Dec. 2000, pp. 1443-1452.
J. Am. Assoc. Gynecol. Laparosc., Feb. 2001, pp. 83-86.
J. Reprod. Med., Jun. 2001, pp. 559-563.

* cited by examiner

RADIATION APPLICATOR

This invention relates to microwave radiators and, in particular, to microwave ablation devices.

A known microwave radiator, used for microwave ablation of tissue, comprises a microwave generator operatively coupled to an elongate waveguide for conveying the microwaves to the ablation site. The waveguide is sufficiently thin to be inserted into the body and contains a core of dielectric material which enables efficient transmission of microwaves through the waveguide. At the emission end of the waveguide, the dielectric core protrudes and provides a radiating tip for coupling microwaves into surrounding tissue. An object of the inventor is to provide an improved radiator.

According to one aspect, the invention includes an elongate microwave radiator for insertion into a living body to treat biological tissue at a predetermined operating frequency, the radiator comprising a monopole at its tip and dielectric material surrounding the monopole; characterised in that said dielectric material is adapted so that it acts as a resonator at said predetermined operating frequency, and encompasses generally the whole of the near-field radiation emitted by the monopole.

The invention is based on an appreciation of the fact that a monopole antenna generates a near-field, and that the near-field contains large field amplitudes which exist quasi-statically in the local region of the monopole and do not radiate energy. In a normal communications antenna, this local region is air-filled and these near-field amplitudes have no effect except to contribute reactance to the antenna impedance. However, in a medical application, if the near-field region contains biological matter, which is highly lossy, the near-field amplitudes will generate heat.

Because of the high amplitudes and small volume of the near-field region, much heat can be generated in the near-field region, which reduces the energy in the far-field. Field penetration is therefore reduced, and local charring in the near-field region becomes a limiting factor in the power that can be input to the antenna.

The dielectric body according to the invention serves to provide a low loss environment to encompass the near-field region so that more power is transmitted to the biological matter in the far-field region.

The extent of the near-field is determined by the wavelength $\lambda$ of the radiation in the dielectric and the length L of the monopole according to the relationship $2L^2/\lambda$. The extent of the near-field therefore is proportional to $\lambda$, and it is possible to reduce the extent of the near-field region by increasing the dielectric constant of the body to reduce the wavelength of the radiation within it. The overall external dimension of the device can therefore be reduced for insertion into a living body. A higher dielectric constant will also accommodate the use of lower frequency radiation, which would otherwise increase the wavelength and the extent of the near-field; the lower frequency radiation being beneficial in increasing radiation penetration into the far-field.

A monopole antenna, for good impedance matching, has L generally equal to $\lambda/2$. By substitution in the above relationship, the extent of the near-field is then equal to $\lambda/2$, and this determines the minimum extent of the dielectric material. Furthermore, a $\lambda/2$ dimension for the dielectric material is consistent with its operation as a resonator to ensure that the radiator is effective in transmitting radiation at the required power levels for the treatment of biological material.

In one embodiment of the invention, the dielectric body comprises a cylindrical shape with the monopole extending axially along its center. A radiator of this kind can be designed with a minimum radius for insertion into biological matter, such as a liver, and will create an annular radiation field around it. A pointed tip may be provided at the free end of the dielectric material to assist penetration of biological matter.

As the dielectric constant is increased, it may exceed that of the biological matter, which can lead to total internal reflection of radiation within the dielectric and a consequent reduction in transmitted radiation. In order to overcome this problem, the dielectric body is formed so that the dielectric constant at its core is higher than that at its outer periphery, the latter having a value intermediate that of the core and the biological matter. Thus, the dielectric constant at the core may be higher than that of the surrounding biological matter so as to help reduce the overall diameter of the radiator. The different dielectric constants may correspond to different layers of dielectric, each with a different dielectric constant, or may correspond to different levels in a dielectric in which the dielectric constant varies throughout its depth.

According to another aspect, the invention an elongate microwave radiator for insertion into a living body, to treat biological tissue at a predetermined operating frequency, the radiator comprising a monopole at its tip and dielectric material surrounding and extending beyond the monopole; characterised in that said dielectric material terminates in a rounded tip portion and is adapted so that it acts as a resonator at said predetermined operating frequency and enhances transmission of radiation in the forward direction.

Preferably, the tip portion is generally hemispherical and has a radius generally equal to half a wavelength of the radiation in the dielectric material.

The radiator may further comprise a coaxial conductor (preferably packed with a dielectric) which supplies radiation to the monopole antenna from a radiation generator. Preferably, the monopole then comprises an exposed length of the central conductor of the coaxial conductor at its distal end. Preferably, the exposed length of the central conductor providing the monopole, is generally half the wavelength of the radiation in the dielectric. The coaxial conductor may be rigid or a flexible cable.

Preferably, the dielectric material has a dielectric constant, or relative permittivity, such that the length of the monopole is reduced. Advantageously, there can be a transformer between the coaxial conductor and the dielectric material to reduce reflection of radiation back into the coaxial conductor from the boundary between it and the dielectric material. Such a transformer can advantageously contain a space into which the dielectric packing of the coaxial conductor can expand.

According to yet another aspect, the invention includes methods of coupling radiation into biological material using the devices according to the invention.

Further advantages and features of the invention will become apparent to readers skilled in the art upon consideration of the following description of embodiments of the invention, the embodiments being described by way of example only, and with reference to the accompanying figures, in which.

Figure 1:
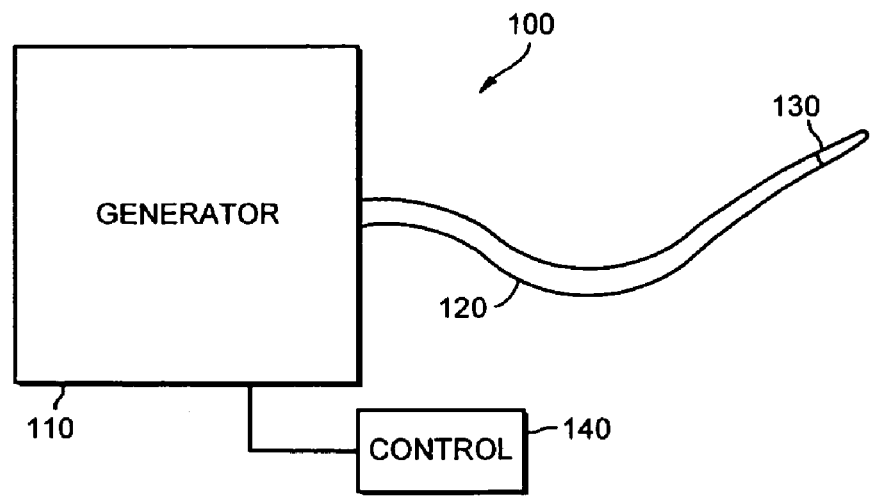
FIG. 1 shows a first embodiment of a radiator according to the invention.

FIG. 1 shows the general arrangement of the microwave radiator 100. A radiation generator 110, for example, a microwave generator, produces radiation which is coupled into coaxial cable 120 which transmits the radiation to a distal tip region 130 at which there is an antenna for emitting the radiation into the material surrounding the tip 130. In use, the coaxial cable 120 is introduced into a living body and the tip 130 is positioned adjacent a region which it is desired to irradiate. For example, the device could be inserted into an artery to irradiate plaques on the walls thereof or the device could be introduced into a uterus to irradiate the endometrium. The supply of radiation is controlled by a control device 140, often a foot pedal, which is used to signal the microwave generator to begin, adjust or stop the supply of radiation to the tip 130.

Figure 2:
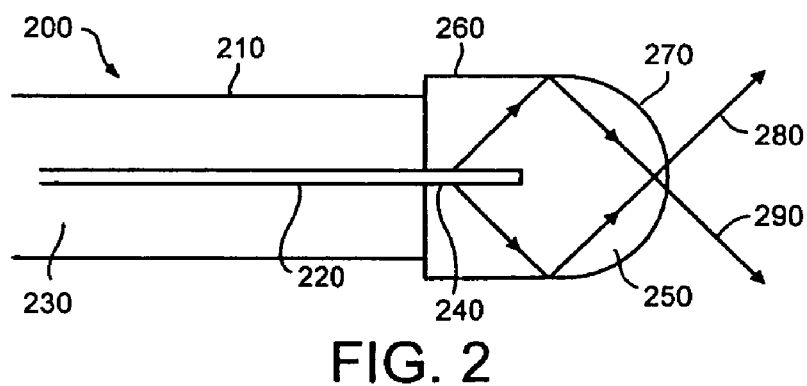
FIG. 2 shows the tip section of a radiator of FIG. 1 in more detail.

FIG. 2 shows the tip region 130 of the radiator of FIG. 1 in more detail. The tip region, generally indicated 200, shows the distal end of the coaxial cable which comprises an outer conductor 210 spaced from a core conductor 220. The space between the conductors 210 and 220 is filled with a dielectric material 230. The antenna for emitting radiation conducted by the cable comprises a length 240 of the core conductor of the coaxial cable extending beyond the outer conductor 210 at the distal end of the coaxial cable to form a monopole. To enhance the radiating qualities of the monopole 240, it is preferred that its length is about one half of a wavelength of the radiation in the dielectric. The monopole 240 is enveloped by dielectric body 250 in which the wavelength of the employed radiation is reduced below its free-space value hence enabling the monopole to be shorter than might otherwise be possible. The dielectric body 250 comprises a cylindrical portion 260 which envelops the monopole 240. The diameter of the cylindrical portion 260 is generally equal to the wavelength of the radiation in the dielectric at the operating frequency so that it is tuned to act as a resonator to increase the power it radiates. Also, the dielectric body comprises a hemispherical section 270 which supports partial internal reflection of the radiation from the antenna in the forward direction as indicated by arrows 280 and 290. The hemispherical section 270 is dimensioned so as to provide a resonator which further enhances radiation from the dielectric body in 250 in the forward direction. Resonance of radiation partially reflected within the dielectric body 250 can be encouraged by, for example, dimensioning the hemispherical section 270 to have a radius approximately equal to one half of a wavelength of the radiation employed. It will be appreciated that the dielectric body can have other dimensions and shapes provided that they encourage forward propagation of the radiation by means of internal reflection and/or resonance.

When this equipment is to be used for endometrial ablation it is desirable to use radiation having a frequency around 9.2 GHz. In free-space, the wavelength of such radiation is about 32 mm. Using dielectric material with, for example, a dielectric constant $\epsilon_R=25$ reduces the wavelength to about 6 mm. Correspondingly, the diameter and overall length of the dielectric material are then also about 6 mm.

Figure 3:
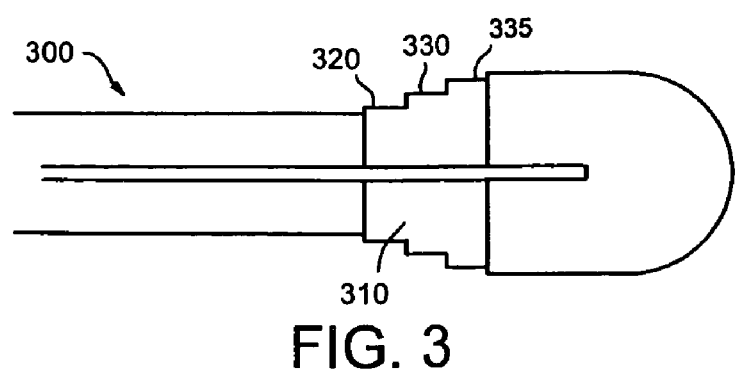
FIG. 3 shows a second embodiment of the tip section of the radiator incorporating a transformer.

FIG. 3 shows an alternative embodiment of the tip section of the radiator, generally indicated 300. Here, in order to reduce reflection of radiation from the coaxial cable at the boundary between it and the dielectric material, a transformer 310 is incorporated between the coaxial cable and the dielectric material. The transformer 310 comprises several sections (for example, three: 320, 330, 340) of cylindrical shape and of successively increasing radius towards the dielectric material. Advantageously, at least the section 320 of the transformer adjacent the coaxial cable does not contain a solid filler material. This provides the benefit that, when the radiator is heated, for example in manufacture or in use, the dielectric packing filling the space between the core and outer conductors of the coaxial cable can expand into the transformer thus relieving otherwise deleterious pressures.

The near-field radiation generated by the radiator of FIGS. 2 and 3 extends from the monopole 240 a distance determined by the formula $2L^2/\lambda$, where L is the length of the monopole, and $\lambda$ is the wavelength of the radiation in the dielectric material 250. However, the preferred value of L is $\lambda/2$, and therefore the near-field radiation is contained within a region of radius $\lambda/2$ about the monopole. Therefore, the near-field radiation does not extend into the more lossy biological material that surrounds the radiators in use, and the resulting detrimental affects of local charring and reduction of radiation penetration are reduced or avoided. Instead, the microwave power is emitted into the far-field to increase penetration and power transfer.

Figure 4:
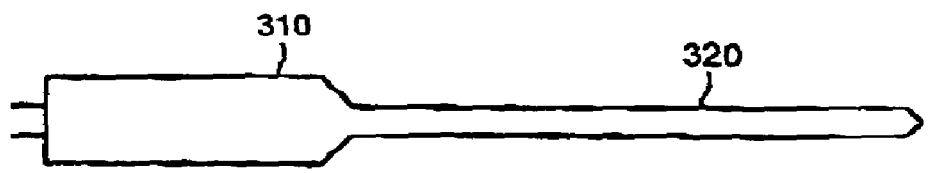
FIG. 4 shows a third embodiment of the radiator.
Figure 5:
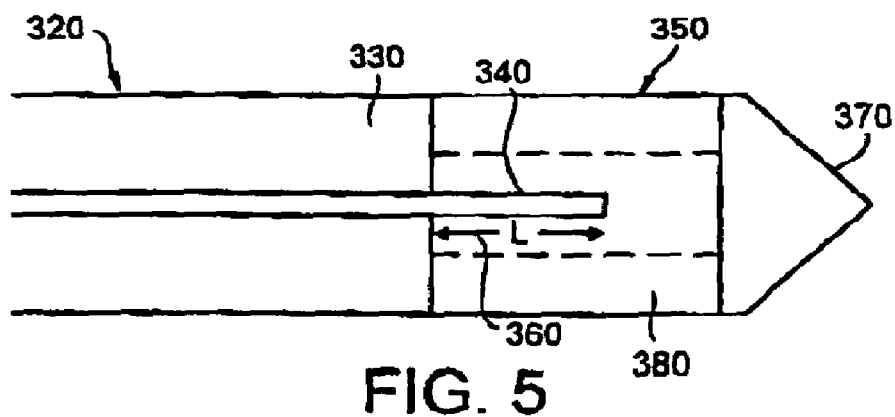
FIG. 5 shows the tip of the radiator of FIG. 4.
Figure 6:
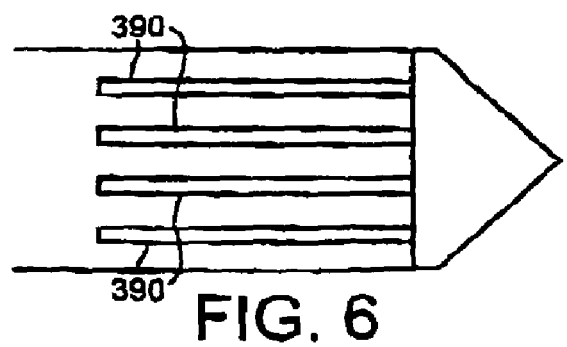
FIG. 6 shows a side-elevation of a variation in design of the radiator of FIG. 4.

FIG. 4 shows yet another embodiment of the invention in which a generator 310 supplies microwave energy via a rigid coaxial conductor 320 to a tip region at the distal end of the conductor. Dielectric packing 330 is provided between the inner and outer conductors of the coaxial conductor 320. As shown in more detail in FIG. 5, a length of the inner conductor 340 at the tip is exposed by removal of the outer conductor so as to form monopole to emit radiation. The monopole 340 is embedded axially in a cylindrical body of dielectric 350 which has substantially the same outer diameter as the coaxial conductor 320. A pointed metal tip 370 is fixed to the end of the dielectric 350 and serves to assist penetration into biological matter, such as a liver to perform ablation on a tumour. The monopole 340 preferably has a length substantially equal to half a wavelength of the radiation in the dielectric, and the radius of the dielectric body 350 is also preferably substantially equal to half a wavelength of the radiation in the dielectric. The near-field radiation emitted by the monopole will then lie within a region $2L^2/\lambda$, which is equal to a radius of half of the wavelength of the radiation in the dielectric so that the near-field lies substantially totally within the dielectric. The dielectric constant of the dielectric body is selected to be high so as reduce losses within the dielectric. The microwave energy is therefore emitted into the far-field region in an annular pattern around the tip so as to increase field penetration and power transfer. Typically, a radiation applicator used with a generator operating at 10 GHz and having a dielectric body with dielectric constant $\epsilon_R=25$, will have a dielectric body radius of 3 mm. Because the radius of the dielectric body 350 is substantially equal to half a wavelength, it is tuned to act as a resonator, which increases the power it radiates.

The invention claimed is:

1. An elongate microwave radiator for insertion into a living body to treat biological tissue at a predetermined operating frequency, the radiator comprising a monopole antenna at its tip, the monopole antenna comprising:

a monopole; and dielectric material surrounding the monopole the dielectric material being configured to act as a resonator at said predetermined operating frequency, and encompassing generally the whole of the near-field radiation emitted by the monopole, in which the dielectric material of the monopole antenna is such that it has a dielectric constant at its core which is higher than the dielectric constant at its outer periphery, the latter being more closely matched to that of said biological tissue.

2. A radiator as claimed in claim 1 in which the dielectric material of the monopole antenna comprises an inner core and an outer layer, each of a different dielectric constant.

3. A radiator as claimed in claim 2 in which the inner core and outer layer have those dimensions that extend from the monopole of the monopole antenna, which are determined in accordance with the dielectric constant of each so that the overall dimension is a predetermined fraction of the nominal wavelength of the radiation in the dielectric.

4. A radiator as claimed in claim 3 in which the inner core and outer layer each have a dimension generally equal to a quarter of the wavelength of radiation therein.

5. A radiator as claimed in claim 2 in which the outer layer is formed with indentations in its outer surface which serve to reduce the dielectric constant in this region when the indentations are filled with other matter.

6. A radiator as claimed in claim 1 in which the dielectric constant of the dielectric material of the monopole antenna varies continuously in space over at least a part of the distance from the monopole of the monopole antenna.

7. A radiator as claimed in claim 1 which has a tip portion that extends beyond an end of the monopole of the monopole antenna.

8. A radiator as claimed in claim 7 in which the tip portion is pointed to assist penetration of biological matter.

9. A radiator as claimed in claim 8 in which the tip portion is composed of a different material to the dielectric material.

10. A radiator as claimed in claim 7 in which the tip portion is an extension of the dielectric material and is rounded so as to support forward transmission of radiation.

11. A radiator as claimed in claim 10 in which the tip portion is generally hemispherical.

12. An elongate microwave radiator for insertion into a living body to treat biological tissue at a predetermined operating frequency, the radiator comprising a monopole antenna at its tip, the monopole antenna comprising:
 a monopole; and
 dielectric material surrounding the monopole, the dielectric material being configured to act as a resonator at said predetermined operating frequency, and encompassing generally the whole of the near-field radiation emitted by the monopole,
 in which the elongate device comprises a coaxial conductor with a central conductor that projects beyond outer screening of the coaxial conductor at the distal end to form the monopole of the monopole antenna, and
 further including a transformer between the coaxial conductor and the dielectric material to reduce reflection of radiation back into the coaxial conductor at the boundary with the dielectric material.

13. A radiator as claimed in claim 12 in which the transformer includes a space within the coaxial conductor into which packing of the coaxial conductor can expand.

14. A radiator as claimed in claim 12 which has a tip portion that extends beyond an end of the monopole of the monopole antenna.

15. A radiator as claimed in claim 14 in which the tip portion is pointed to assist penetration of biological matter.

16. A radiator as claimed in claim 15 in which the tip portion is composed of a different material to the dielectric material.

17. A radiator as claimed in claim 14 in which the tip portion is an extension of the dielectric material and is rounded so as to support forward transmission of radiation.

18. A radiator as claimed in claim 17 in which the tip portion is generally hemispherical.

19. A method of coupling radiation into biological material, the radiation being generated by an applicator comprising a monopole antenna including a monopole surrounded by a dielectric body, the method comprising:
 configuring the dielectric body of the monopole antenna to act as a resonator; and
 selecting the dielectric constant of the body in accordance with the wavelength of the radiation in the dielectric so that generally the whole of the near-field of the radiation is encompassed by the dielectric body,
 in which the dielectric constant of the dielectric body varies, and is higher at its core than its outer periphery, and the dielectric constant at its outer periphery is lower than that of the surrounding biological matter.

20. A method of coupling radiation into biological material, the radiation being generated by an applicator comprising a monopole antenna including a monopole surrounded by a dielectric body, the method comprising:
 configuring the dielectric body of the monopole antenna to act as a resonator; and
 selecting the dielectric constant of the body in accordance with the wavelength of the radiation in the dielectric so that generally the whole of the near-field of the radiation is encompassed by the dielectric body, in which
 the dielectric constant of the body is high, but is lower than that of the biological material, and
 the dielectric constant at the core is greater than the dielectric constant of the biological matter.

* * * * *